United States Patent [19]

Tuch

[11] Patent Number: 5,679,400
[45] Date of Patent: Oct. 21, 1997

[54] INTRAVASCULAR STENT AND METHOD

[75] Inventor: Ronald J. Tuch, Plymouth, Minn.

[73] Assignee: Medtronic, Inc., Minneapolis, Minn.

[21] Appl. No.: 482,346

[22] Filed: Jun. 7, 1995

Related U.S. Application Data

[63] Continuation-in-part of Ser. No. 52,878, Apr. 26, 1993, Pat. No. 5,464,650.

[51] Int. Cl.$^6$ ............... B05D 3/00; B05D 1/38; A61J 3/00; A61L 27/00
[52] U.S. Cl. .......... 427/2.14; 427/2.24; 427/352
[58] Field of Search .............. 427/2.24, 2.25, 427/2.28, 2.21, 352, 353, 2.14

[56] References Cited

U.S. PATENT DOCUMENTS

| | | |
|---|---|---|
| 4,292,965 | 10/1981 | Nash et al. . |
| 4,529,614 | 7/1985 | Burns . |
| 4,532,929 | 8/1985 | Mattei et al. . |
| 4,548,736 | 10/1985 | Müller et al. ............ 252/315.1 |
| 4,733,665 | 3/1988 | Palmaz ............. 128/343 |
| 4,753,652 | 6/1988 | Langer et al. ............ 623/1 |
| 4,800,882 | 1/1989 | Gianturco ........... 128/343 |
| 4,869,909 | 9/1989 | Takahashi et al. ........ 427/2.31 |
| 4,886,062 | 12/1989 | Wiktor . |
| 4,888,009 | 12/1989 | Lederman et al. . |
| 4,894,231 | 1/1990 | Moreau et al. ............ 424/426 |
| 4,955,899 | 9/1990 | Della Corna et al. ......... 427/2.25 |
| 5,019,090 | 5/1991 | Pinchuk ............. 606/194 |
| 5,102,417 | 4/1992 | Palmaz ............ 606/195 |
| 5,176,907 | 1/1993 | Leong ............. 424/78.08 |
| 5,192,308 | 3/1993 | Ostapchenko ............ 623/1 |
| 5,221,698 | 6/1993 | Amiden et al. ............ 523/122 |
| 5,234,456 | 8/1993 | Silverstrini ............ 606/194 |
| 5,242,391 | 9/1993 | Place et al. ............ 604/60 |
| 5,290,266 | 3/1994 | Rohling et al. ............ 604/272 |
| 5,295,978 | 3/1994 | Fan et al. ............ 427/2.1 |
| 5,380,299 | 1/1995 | Fearnot et al. ............ 604/265 |
| 5,416,131 | 5/1995 | Wolff et al. ............ 427/2.28 |
| 5,443,496 | 8/1995 | Schwartz et al. ............ 604/890.1 |
| 5,447,724 | 9/1995 | Helmus et al. ............ 427/2.12 |
| 5,510,077 | 4/1996 | Dinh et al. ............ 264/279 |
| 5,558,900 | 9/1996 | Fan et al. ............ 427/2.28 |

FOREIGN PATENT DOCUMENTS

| | | |
|---|---|---|
| 9013332 | 11/1990 | WIPO . |
| 9112779 | 9/1991 | WIPO . |
| 9116102 | 10/1991 | WIPO . |
| 9117789 | 11/1991 | WIPO . |
| 9118940 | 12/1991 | WIPO . |
| 9306792 | 4/1993 | WIPO . |
| 0566245 | 10/1993 | WIPO . |

OTHER PUBLICATIONS

"Seeding of Intravascular Stents with Genetically Engineered Endothelial Cells" by Dicket et al, in Circulation, vol. 80, No. 5 Nov. 1989.
"Restenosis and the Proportinal Neointimal Response to Coronary Artery Injury: Results in a Porcine Model" by Schwartz et al., in JACC, vol. 19, No. 2, Feb. 1992 pp. 267–274.
"Restenosis After Baloon Angioplasty" by Schwartz, et al., in Circulation, vol. 82, No. 6, Dec. 1990.

*Primary Examiner*—Diana Dudash
*Attorney, Agent, or Firm*—Daniel W. Latham; Harold R. Patton

[57] ABSTRACT

A method for making an intravascular stent by applying to the body of a stent a solution which includes a solvent, a polymer dissolved in the solvent and a therapeutic substance dispersed in the solvent and then evaporating the solvent. The inclusion of a polymer in intimate contact with a drug on the stent allows the drug to be retained on the stent during expansion of the stent and also controls the administration of drug following implantation. The adhesion of the coating and the rate at which the drug is delivered can be controlled by the selection of an appropriate bioabsorbable or biostable polymer and the ratio of drug to polymer in the solution. By this method, drugs such as dexamethasone can be applied to a stent, retained on a stent during expansion of the stent and elute at a controlled rate.

11 Claims, 5 Drawing Sheets

INTRAVASCULAR STENT AND METHOD

This is a continuation-in-part of Ser. No.08/052,878 filed Apr. 26, 1993, now U.S. Pat. No. 5,464,650.

BACKGROUND OF THE INVENTION

This invention relates to intravascular stents for treatment of injuries to blood vessels and particularly to stents having a framework onto which a therapeutic substance or drug is applied.

Although angioplasty procedures have increased greatly in popularity for treatment of occluded arteries, the problem of restenosis following the angioplasty treatment remains a significant problem. Restenosis is the closure of a peripheral or coronary artery following trauma to the artery caused by efforts to open an occluded portion of the artery by angioplasty, such as, for example, by balloon dilation, atherectomy or laser ablation treatment of the artery. For these angioplasty procedures, restenosis occurs at a rate of about 30–60% depending upon the vessel location, lesion length and a number of other variables.

One aspect of restenosis may be simply mechanical; e.g. caused by the elastic rebound of the arterial wall and/or by dissections in the vessel wall caused by the angioplasty procedure. These mechanical problems have been successfully addressed by the use of stents to tack-up dissections and prevent elastic rebound of the vessel, thereby reducing the level of restenosis for many patients. The stent is typically inserted by catheter into a vascular lumen and expanded into contact with the diseased portion of the arterial wall, thereby providing internal support for the lumen. Examples of stents which have been successfully applied over a PTCA balloon and radially expanded at the same time as the balloon expansion of an affected artery include the stents disclosed in U.S. Pat. No. 4,733,665 issued to Palmaz, U.S. Pat. No. 4,800,882 issued to Gianturco and U.S. Pat. No. 4,886,062 issued to Wiktor which are incorporated herein by reference in their entirety.

Another aspect of restenosis is believed to be a natural healing reaction to the injury of the arterial wall that is caused by angioplasty procedures. The final result of the complex steps of the healing process is intimal hyperplasia, the migration and proliferation of medial smooth muscle cells, until the artery is again occluded.

To address both aspects of the restenosis problem, it has been proposed to provide stents which are seeded with endothelial cells (Dichek, D. A. et al Seeding of Intravascular Stents With Genetically Engineered Endothelial Cells; Circulation 1989; 80: 1347–1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall include simple heparin-coated metallic stents, whereby a heparin coating is ionically or covalently bonded to the stent. Still other methods of providing therapeutic substances to the vascular wall by means of stents have also been proposed such as in U.S. Pat. No. 5,102,417 issued to Palmaz or in international patent application WO 91/12779 "Intraluminal Drug Eluting Prosthesis" and international patent application WO 90/13332 "Stent With Sustained Drug Delivery". In those applications, it is suggested that antiplatelet agents, anticoagulant agents, antimicrobial agents, antimetabolic agents and other drugs could be supplied in stents to reduce the incidence of restenosis.

Metal stents such as those disclosed in U.S. Pat. No. 4,733,665 issued to Palmaz, U.S. Pat. No. 4,800,882 issued to Gianturco or U.S. Pat. No. 4,886,062 issued to Wiktor could be suitable for drug delivery in that they are capable of maintaining intimate contact between a substance applied to the outer surface of the stent and the tissues of the vessel to be treated. However, there are significant problems to be overcome in order to secure a therapeutically significant amount of a substance onto the metal of the stent; to keep it on the stent during expansion of the stent into contact with the blood vessel wall; and also controlling the rate of drug delivery from the drug on the stent to the vessel wall.

It is therefore an object of the present invention to provide a stent having a therapeutically significant amount of a drug applied thereto.

It is also an object of the present invention to provide a stent which may be delivered and expanded in a selected blood vessel without losing a therapeutically significant amount of a drug applied thereto.

It is also an object of the present invention to provide a drug-containing stent which allows for a sustained release of the drug to vascular tissue.

It is also an object of the present invention to provide a simple method for applying to a stent a coating of a therapeutic substance.

SUMMARY OF THE INVENTION

These and other objects are accomplished by the present invention. We have discovered an intravascular stent having a coating which includes a polymer and a therapeutic substance on the body of a stent, and in particular on its tissue-contacting surface, in which the coating has a greater concentration of therapeutic substance on the portion of the coating nearest the stent body than near the exterior surface of the coating. The inclusion of a polymer in intimate contact with a drug on the stent allows the drug to be retained on the stent in a resilient matrix during expansion of the stent and also slows the administration of drug following implantation. By placing the greater concentration of the drug toward the stent body, control over the rate of administration of the drug is significantly improved. The coating can be applied whether the stent has a metallic or polymeric surface. The coating can also be provided by methods which assure carefully controlled dosage.

In one aspect of the invention, the coating is comprised of a solid/solid solution of polymer and drug. That is, that the drug and polymer are both soluble in the same solvent and have been intimately admixed in the presence of that solvent. The drug and polymer can be applied by simply immersing the stent into the solution or by spraying the solution onto the stent. The total amount of drug to be included on the stent can be readily controlled by applying multiple thin coats of the solution while allowing it to dry between coats. For example, a target dosage of drug is determined and the stent body is weighed. A solution of polymer, drug and solvent having a predetermined weight ratio of polymer to drug is applied to the stent body in successive thin coats with drying and weighing of the stent between coats. When the total weight of coating on the stent multiplied by the weight ratio of drug in the coating indicates that the target dosage has been achieved, no additional drug/polymer solution is applied. The overall coating should be thin enough so that it will not significantly increase the profile of the stent for intravascular delivery by catheter. It is therefore preferably less than about 0.002 inch thick and most preferably less than 0.001 inch thick. The adhesion of the coating and the rate at which the drug is delivered can be controlled by the selection of an appropriate bioabsorbable or biostable polymer and by the ratio of drug to polymer in the solution. By this method, drugs such as glucocorticoids (e.g. dexamethasone, betamethasone), heparin, hirudin, tocopherol, angiopeptin, aspirin, ACE inhibitors, growth factors, oligonucleotides, and, more generally, antiplatelet agents, anticoagulant agents, antimitotic agents, antioxidants, antimetabolite agents, and anti-inflammatory agents can be applied to a stent, retained on a stent during expansion of the stent and elute the drug at a controlled rate.

The release rate of the solid/solid solution of polymer and drug is further controlled by varying the ratio of drug to polymer in the multiple layers. For example, a higher drug-to-polymer ratio in the inner layers than in the outer layers would result in a lower initial dose and a total dose which would be delivered more evenly and over a much longer period of time. In the solid/solid solution of polymer and drug, this can be accomplished while maintaining the correct therapeutic dosage by applying to a stent which already has a coating containing a desired amount of drug, a thin coating overlayer or several thin overlayers of the same polymer and solvent without the drug while drying the stent between each coating layer. Since both the drug and polymer are soluble in the solvent, the drug and polymer are dissolved slightly in the application of each of the coating overlayers which creates a concentration gradient of drug in the overlayers that is sharply reduced from that in the main coating nearest the stent body.

In another aspect of the invention, the coating need not be a solid/solid solution of polymer and drug, but may instead be provided from any combination of drug and polymer applied to the stent. The coating is provided with a greater concentration of drug on the portion of the coating nearest the stent body by pre-eluting the stent. That is, a solution of solvent and polymer together with a dissolved or dispersed drug is applied to a stent body as set forth above to a desired amount of drug on the stent. The stent is then immersed into a solution which has a greater solubility for the drug than for the polymer. For example, water or a saline solution may be used. The stent remains in the solvent for a pre-defined period of time under controlled conditions such that a known quantity of the drug is eluted from the stent. The stent is then dried, sterilized and packaged with the desired amount of drug remaining on the stent.

In operation, the stent made according to the present invention can deliver drugs to a body lumen by introducing the stent transluminally into a selected portion of the body lumen and radially expanding the stent into contact with the body lumen. The transluminal delivery can be accomplished by a catheter designed for the delivery of stents and the radial expansion can be accomplished by balloon expansion of the stent, by self-expansion of the stent, or a combination of serf-expansion and balloon expansion.

DETAILED DESCRIPTION OF THE INVENTION

The present invention relates to a method for making an intravascular stent. The underlying structure of the stent can be virtually any stent design, whether of the self-expanding type or of the balloon-expandable type and whether metal or polymeric. Thus metal stent designs such as those disclosed in U.S. Pat. No. 4,733,665 issued to Palmaz, U.S. Pat. No. 4,800,882 issued to Gianturco or U.S. Pat. No. 4,886,062 issued to Wiktor could be used in the present invention. The stent could be made of virtually any bio-compatible material having physical properties suitable for the design. For example, tantalum and stainless steel have been proven suitable for many such designs and could be used in the present invention. Also, stents made with biostable or bioabsorbable polymers such as poly(ethylene terephthalate), polyacetal, poly(lactic acid), poly(ethylene oxide)/poly (butylene terephthalate) copolymer could be used in the present invention. Although the stent surface should be clean and free from contaminants that may be introduced during manufacturing, the stent surface requires no particular surface treatment in order to retain the coating applied in the present invention. Both the inner and outer surfaces of the stent may be provided with the coating according to the present invention.

In order to provide the coated stent according to the present invention, a solution which includes a solvent, a polymer dissolved in the solvent and a therapeutic substance dispersed in the solvent is first prepared. It is important to choose a solvent, a polymer and a therapeutic substance that are mutually compatible. It is essential that the solvent is capable of placing the polymer into solution at the concentration desired in the solution. It is also essential that the solvent and polymer chosen do not chemically alter the therapeutic character of the therapeutic substance. However, the therapeutic substance only needs to be dispersed throughout the solvent so that it may be either in a true solution with the solvent or dispersed in fine particles in the solvent. Examples of some suitable combinations of polymer, solvent and therapeutic substance are set forth in Table 1 below.

TABLE 1

| POLYMER | SOLVENT | THERAPEUTIC SUBSTANCE |
| --- | --- | --- |
| poly(L-lactic acid) | chloroform | dexamethasone |
| poly(L-lactic acid) | chloroform | colchicine |
| poly(lactic acid-co-glycolic acid) | acetone | dexamethasone |
| polyether urethane | N-methyl pyrrolidone | tocopherol (vitamin E) |
| silicone adhesive | xylene | dexamethasone phosphate |
| poly(hydroxy-butyrate-co-hydroxyvalerate) | dichloromethane | aspirin |
| fibrin | water (buffered saline) | heparin |

The solution is applied to the stent and the solvent is allowed to evaporate, thereby leaving on the stent surface a coating of the polymer and the therapeutic substance.

Typically, the solution can be applied to the stent by either spraying the solution onto the stent or immersing the stent in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the stent. In either a coating applied by spraying or by immersion, multiple application steps are generally desirable to provide improved coating uniformity and improved control over the amount of therapeutic substance to be applied to the stent.

The polymer chosen must be a polymer that is biocompatible and minimizes irritation to the vessel wall when the stent is implanted. The polymer may be either a biostable or a bioabsorbable polymer depending on the desired rate of release or the desired degree of polymer stability, but a bioabsorbable polymer is probably more desirable since, unlike a biostable polymer, it will not be present long after implantation to cause any adverse, chronic local response. Bioabsorbable polymers that could be used include poly(L-lactic add), polycaprolactone, poly(lactide-co-glycolide), poly(hydroxybutyrate), poly(hydroxybutyrate-co-valerate), polydioxanone, polyorthoester, polyanhydride, poly (glycolic acid), poly(D,L-lactic acid), poly(glycolic acid-co-trimethylene carbonate), polyphosphoester, polyphosphoester urethane, poly(amino acids), cyanoacrylates, poly (trimethylene carbonate), poly(iminocarbonate), copoly (ether-esters) (e.g. PEO/PLA), polyalkylene oxalates, polyphosphazenes and biomolecules such as fibrin, fibrinogen, cellulose, starch, collagen and hyaluronic add. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The ratio of therapeutic substance-to polymer in the solution will depend on the efficacy of the polymer in securing the therapeutic substance onto the stent and the rate at which the coating is to release the therapeutic substance to the tissue of the blood vessel. More polymer may be needed if it has relatively poor efficacy in retaining the therapeutic substance on the stent and more polymer may be needed in order to provide an elution matrix that limits the elution of a very soluble therapeutic substance. A wide ratio of therapeutic substance to polymer could therefore be appropriate and could range from about 10:1 to about 1:100.

The therapeutic substance used in the present invention could be virtually any therapeutic substance which possesses desirable therapeutic characteristics for application to a blood vessel. This can include both solid substances and liquid substances. For example, glucocorticoids (e.g. dexamethasone, betamethasone), heparin, hirudin, tocopherol, angiopeptin, aspirin, ACE inhibitors, growth factors, oligonudeotides, and, more generally, antiplatelet agents, anticoagulant agents, antimitotic agents, antioxidants, antimetabolite agents, and anti-inflammatory agents could be used. Antiplatelet agents can include drugs such as aspirin and dipyridamole. Aspirin is classified as an analgesic, antipyretic, anti-inflammatory and antiplatelet drug. Dypridimole is a drug similar to aspirin in that it has anti-platelet characteristics. Dypridimole is also classified as a coronary vasodilator. Anticoagulant agents can include drugs such as heparin, coumadin, protamine, hirudin and tick anticoagulant protein. Antimitotic agents and antimetabolite agents can include drugs such as colchicine, methotrexate, azathioprine, vincristine, vinblastine, fluorouracil, adriamycin and mutamycin. Taking colchicine for example, colchicine is an ancient drug which was tested for restenosis reduction by systentic administration without favorable results (see O'Keefe, J H, et al. "Ineffectiveness of Colchicine in the Prevention of Restenosis after Coronary Angioplasty," JACC 1992; 19(7); 1597–1600). Given its unsuccessful use in systentic administration, it was also tested by local administration with the stent coating of the present invention to determine its efficacy.

In the present invention, the intravascular stent includes a coating which includes a polymer and a therapeutic substance on the body of a stent, and in particular on its tissue-contacting surface in which the coating has a greater concentration of therapeutic substance on the portion of the coating nearest the stent body than near the exterior surface of the coating. By placing the greater concentration of the drug toward the stent body, control over the rate of administration of the drug is significantly improved.

Figure 3:
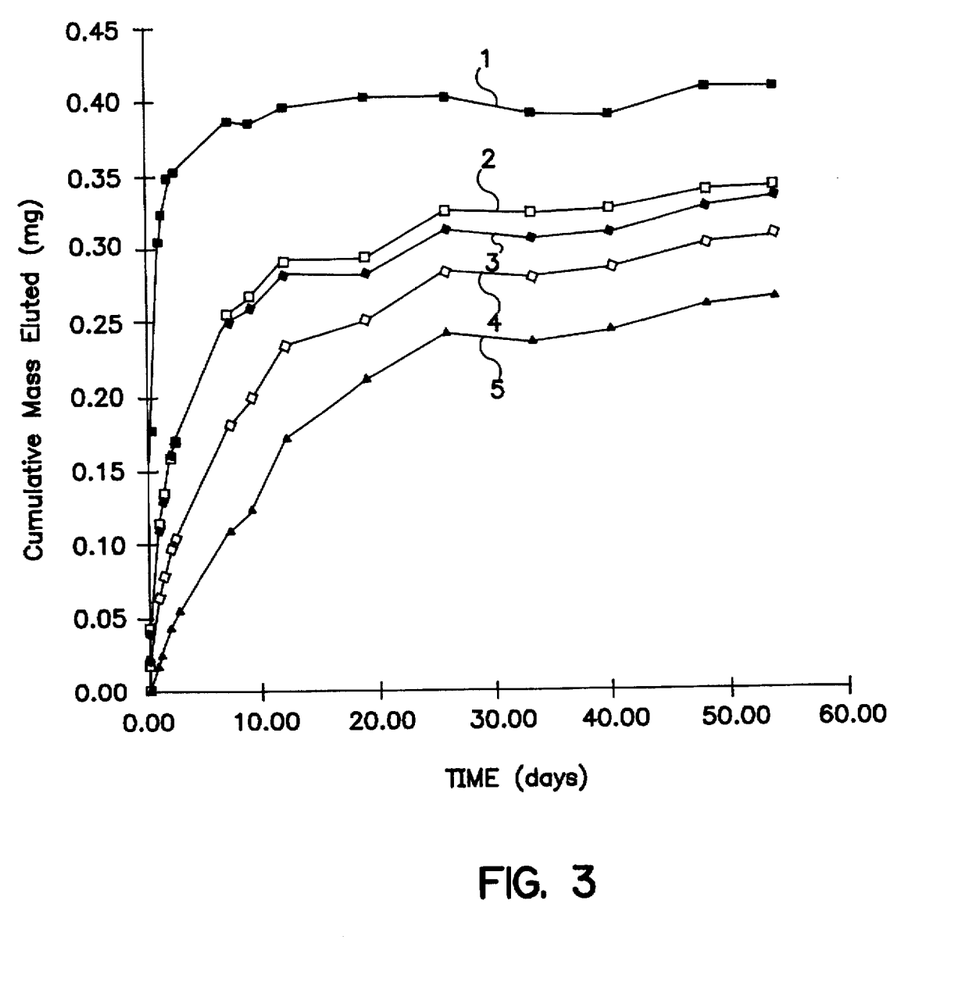
FIG. 3 is a graph showing elution profiles for stents coated with colchicine and poly(L-lactic acid) which have an overlayer of poly(L-lactic acid).

For example, a higher drug-to-polymer ratio in the inner layers than in the outer layers would result in a lower initial dose and a total dose which would be delivered more evenly and over a much longer period of time. In the solid/solid solution of polymer and drug of poly (L-lactic acid) and colchicine, this can be accomplished while maintaining the correct therapeutic dosage by applying to a stent which already has a coating containing a desired amount of colchicine a thin coating layer or several thin overlayers of the same poly (L-lactic acid) polymer and chloroform solvent without the colchicine while drying the stent between each coating layer. Since both the colchicine and poly (L-lactic acid) are soluble in the chloroform, the colchicine and poly (L-lactic acid) already on the stent body are dissolved slightly in the application of each of the coating overlayers which creates a concentration gradient of colchicine in the overlayers that is sharply reduced from that in the main coating nearest the stent body. The effect of this is to alter the drug delivery profile for the stent such as that shown in FIG. 3. In FIG. 3, a coating of 20% colchicine/poly(L-lactic acid) was coated with different overlayer thicknesses. In the curve given by reference numeral 1, an overlayer was provided only on one end of the stent. In the curve given by curve 2, an overlayer was given to the entire stent. In curve 3, the same coating thickness was applied as for curve 2 while in curves 4, and 5 coatings two times as thick and six times as thick respectively were applied. The effect of these overlayers was to dramatically decrease the rate at which the colchicine eluted such that the colchicine did not completely elute out of the stent after the first few days.

It has also been found that the overlayer described above can be made porous. Contrary to expectations, it has been found that the porous overlayer can reduce rather than increase the rate of drug elution. While not wishing to be bound by theory, it is believed that the porous overlayer is less susceptible to cracking as the stent undergoes deformation during handling and implantation. For example, with a Wiktor type stent, the coating is applied to a stent which is in an expanded form. Once the coating is dried, the stent is crimped onto a delivery balloon which causes various stent elements and the coating to bend. During implantation, the delivery balloon expands, again deforming the stent elements and coating. In a very uniform overlayer made with materials which have little elasticity, the overlayer can sustain significant cracking during such deformation. These cracks can then act as channels for more rapid elution of drugs from the drug-rich base coating.

It has been found that cracking of the overlayer can be reduced and drug elution times increased by providing a porous overlayer on the stent. A suitable porous coating can be provided, for example, by phase inversion precipitation of the polymer in the overlayer. According to this technique, a solution of a polymer is prepared in a mixture of two miscible solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous structure. For example, when using poly(L-lactic acid) as the polymer, a suitable solvent composition can include about a 40/60%(w/w) isooctane/ chloroform solution. This solution should be mixed carefully to avoid precipitation during the mixing process. The better solvent for the polymer should dissolve the polymer first (i.e. a solution of poly(L-lactic acid) and chloroform should be made first). A mixture of the solvents should then be added to the polymer solution to bring the ingredients to the desired concentration (i.e. a mixture of isooctane and chloroform is added to the poly(L-lactic add) solution). This mixture is then applied to the stent in the same manner as set forth above. It will be appreciated by those skilled in the art that the nature of the ingredients and the relative concentrations of the ingredients will determine the size of pores. Phase inversion precipitation techniques are well known in the manufacture of porous polymeric membranes. (See e.g. van de Witte et at, *Polyactide Membranes; Correlation between phase transitions and morphology*, doctoral thesis, CIP-GEGEVENS KONINKLIJKE BIBLIOTHEEK, DEN HAAG, 1994).

The following examples are exemplary of various aspects of the invention.

EXAMPLE 1

A 1% solution of dexamethasone in acetone was made, forming a clear solution. The solution was placed in an airbrush reservoir (Badger #200). Wiktor type tantalum wire stents were sprayed with the solution in short bursts while rotating the stents. The acetone quickly evaporated from the stents, leaving a white residue on the stent wire. The process was continued until all of the stent wires were coated. The drug elution rate for the stent was determined by immersing the stent in phosphate buffered saline solution (pH=7.4). Traces of dexamethasone were observed to remain on the immersed stents for less than 31 hours.

EXAMPLE 2

A 2% solution of dexamethasone in acetone was made, forming a solution with suspended particles of dexamethasone. The solution was placed into a tube. Wiktor type tantalum wire stents were dipped rapidly and were allowed to dry. Each stent was dipped into the solution 12–15 times to provide a white surface coating. Two stents were placed on an angioplasty balloon and were inflated on the balloon. Approximately 80% of the dexamethasone coating flaked off of the stents.

EXAMPLE 3

A solution of 1% dexamethasone and 0.5% poly (caprolactone) (Aldrich 18,160-9) in acetone was made. The solution was placed into a tube. Wiktor type tantalum wire stents were dipped rapidly and were allowed to dry. Each stent was dipped into the solution 12–15 times to provide a white surface coating. A stent so coated was expanded on a 3.5 mm angioplasty balloon causing a significant amount of the coating to become detached.

EXAMPLE 4

A solution of 1% dexamethasone and 0.5% poly(lactic acid-co-glycolic acid) (Medisorb) in acetone was made. The solution was placed into a tube. Wiktor type tantalum wire stents were dipped rapidly and were allowed to dry. Each stent was dipped into the solution 12–15 times to provide a white surface coating. A stent so coated was expanded on a 3.5 mm angioplasty balloon causing only a small portion of the coating (less than 25%) to become detached)

EXAMPLE 5

A solution including a 2% dispersion of dexamethasone and a 1% solution of poly(L-lactic acid) (CCA Blochem MW=550,000) in chloroform was made. The solution was placed into an airbrush (Badger). Wiktor type tantalum wire stents were sprayed in short bursts and were allowed to dry. Each stent was sprayed with the solution about 20 times to provide a white surface coating. A stent so coated was expanded on a 3.5 mm angioplasty balloon. The coating remained attached to the stent throughout the procedure.

EXAMPLE 6

Figure 1:
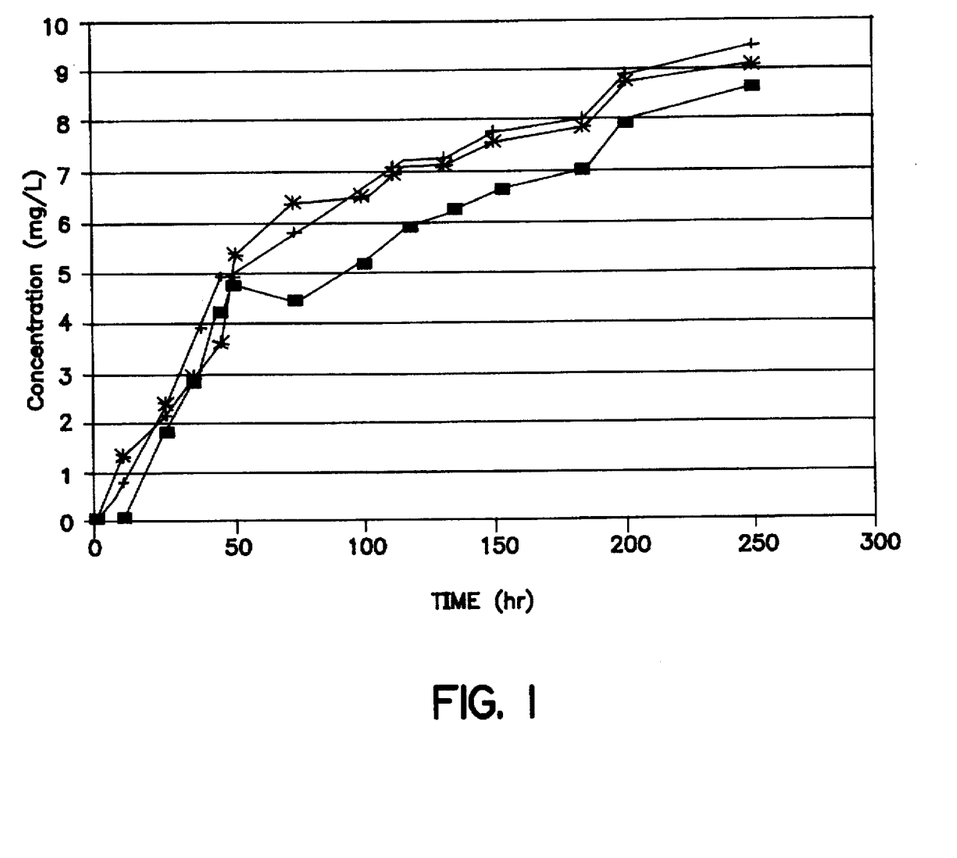
FIG. 1 is a plot showing elution profiles for stents with a coating of dexamethasone and poly(L-lactic acid) made according to Example 6.

A solution including a 2% dispersion of dexamethasone and a 1% solution of poly(L-lactic acid) (CCA Blochem MW=550,000) in chloroform was made. The solution was placed into an airbrush (Badger #250-2). Wiktor type tantalum wire stents were suspended from a fixture and sprayed in 24 short bursts (6 bursts from each of the four directions perpendicular to the stent axis) and were allowed to dry. The resulting stents had a coating weight of about 0.0006–0.0015 grams. Three of the stents were tested for long term elution by placing one stent in 3.0 ml of phosphate buffered saline solution (pH=7.4) at room temperature without stirring. The amount of dexamethasone eluted was evaluated by measuring absorbance at 244 nm in a UV-VIS spectrophotometer. The results of this test are given in FIG. 1.

EXAMPLE 7

Figure 2:
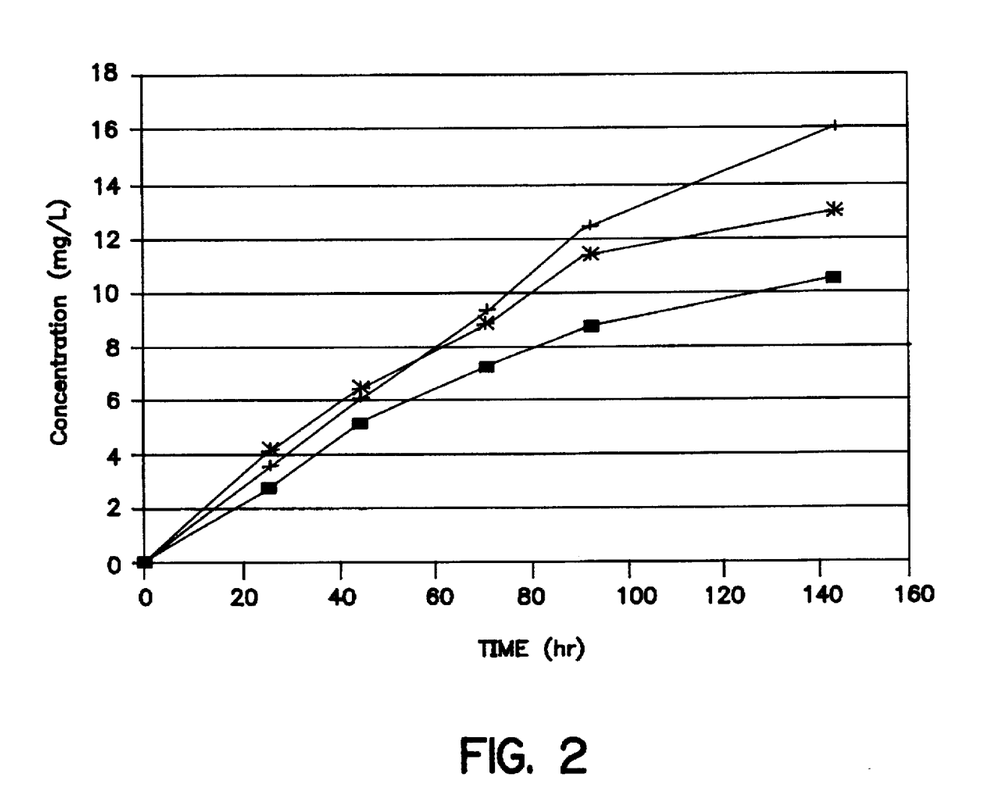
FIG. 2 is a plot showing elution profiles for sterilized stents with a coating of dexamethasone and poly(L-lactic acid) made according to Example 7.

A solution including a 2% dispersion of dexamethasone and a 1% solution of poly(L-lactic acid) (Medisorb 100-L) in chloroform was made along with a control solution of 1% of poly(L-lactic acid) (Medisorb 100-L) in chloroform. The solutions was placed into an airbrush (Badger #250-2). Wiktor type tantalum wire stents were expanded on a 3.0 mm balloon, suspended from a fixture and sprayed in 16 short bursts (2–3 bursts of about 1 second followed by several minutes drying time between applications). The resulting dexamethasone-coated stents had an average coating weight of about 0.0012 grams while the polymer-coated stents had an average polymer weight of about 0.0004 grams. The stents were sterilized in ethylene oxide. Three of the sterilized dexamethasone-coated stents were tested for long term elution by placing one stent in 3.0 ml of phosphate buffered saline solution (pH=7.4) at room temperature without stirring. The amount of dexamethasone eluted was evaluated by measuring absorbance at 244 mn in a UV-VIS spectrophotometer. The results of this test are given in FIG. 2. Dexamethasone-coated stents and polymer-coated control stents were implanted in the coronary arteries of 8 pigs (N=12 for each type) according to the method set forth in "Restenosis After Balloon Angioplasty—A Practical Proliferative Model in Porcine Coronary Arteries," by Robert S. Schwartz, et al, Circulation 82(6):2190–2200, Dec. 1990, and "Restenosis and the Proportional Neointimal Response to Coronary Artery Injury: Results in a Porcine Model" by Robert S. Schwartz et al, *J Am Coll Cardiol*; 19; 267–74 Feb. 1992 with the result that when compared with the controls, the dexamethasone-coated stents reduced the amount of proliferation associated with the arterial injury.

EXAMPLE 8

Stents were coated with colchicine and poly(L-lactic add)formulations for in vivo testing. Solutions of poly(L-lactic acid) and colchicine in chloroform were prepared and mixed to provide a desired percentage of colchicine in the coating with the poly(L-lactic acid) content of the solution maintained at about 1%. The solutions was placed into an airbrush (Badger #250-2). Wiktor type tantalum wire stents were expanded on a 3.0 mm balloon, suspended from a fixture and sprayed in short bursts (bursts of about 1 second). After an mount of colchicine had been applied to each stent, the stents were dried in air for at least about thirty minutes and then further dried in a vacuum drying oven at about 80° C. The stents were removed from the drying oven and weighed. Any difference between the target weight of colchicine to be applied to each stent and the actual weight of colchicine on the stent was noted and the number of additional bursts needed to bring each stent to target weight was estimated. Any weight-deficient stents were then brought up to target weight by the application of additional bursts of the solution. Any recoated stents were then dried and weighed again. A 1% solution of poly(L-lactic acid) in chloroform was used to provide an overlayer to the colchicine-coated stents. A desired number of bursts of the solution (i.e. bursts of about 1 second with preferably a drying time of about 4 seconds between bursts) was applied by spraying in the same manner as the application of the base coating and were dried and weighed. The average amounts of drug and overlayer are given in Table 2.

TABLE 2

| Lot | % drug | Drug Mass (mg) | Overlayer Mass (mg) |
|---|---|---|---|
| 1 | 35 | 1.39 | 0.78 |
| 2 | 25 | 1.03 | 2.42 |
| 3 | 25 | 0.58 | 1.29 |
| 4 | 15 | 0.21 | 1.16 |
| 5 | 10 | 0.10 | 0.55 |
| 6 | 15 | 0.21 | 1.22 |
| 7 | 10 | 0.10 | 0.61 |

The stents were then packaged and gas sterilized.

EXAMPLE 9

Stents were provided with an overlayer of porous poly (L-lactic add) by a phase inversion precipitation technique. A 40/60% (w/w) isooctane/chloroform solution was used containing 0.5% poly(L-lactic add). The solution was made by adding 2.0 g of a solution of 5.0% Poly(L-lactic acid) in chloroform to a pre-mixed solution of 8.0 g isooctane and 10.0 g chloroform. An airbrush apparatus (Badger #250-2) was used to apply the solution to Wiktor stents under the following conditions:

Air pressure=30 psi

Burst duration=0.5 second

Nozzle to stent distance=30 mm

Time between bursts=5–7 seconds (coating turns white)

Ambient temperature and humidity

Figure 4A:
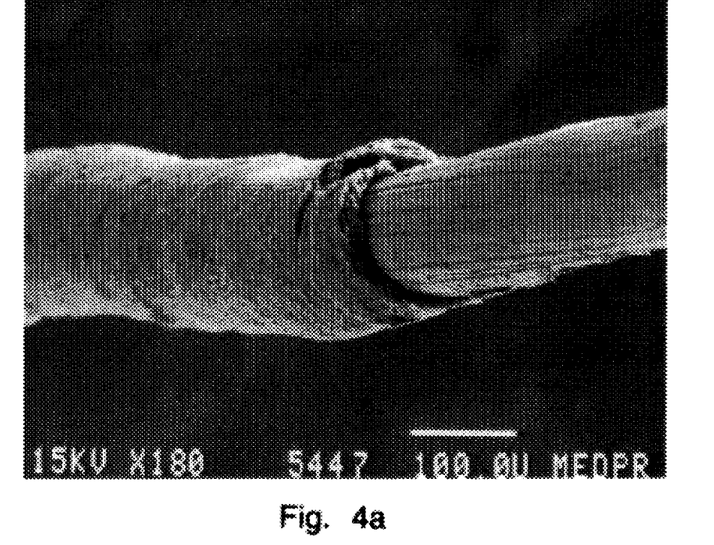
FIGS. 4a, 4b and 4c are SEM micrographs of a porous poly(L-lactic acid) overlayer applied to a stent.
Figure 4B:
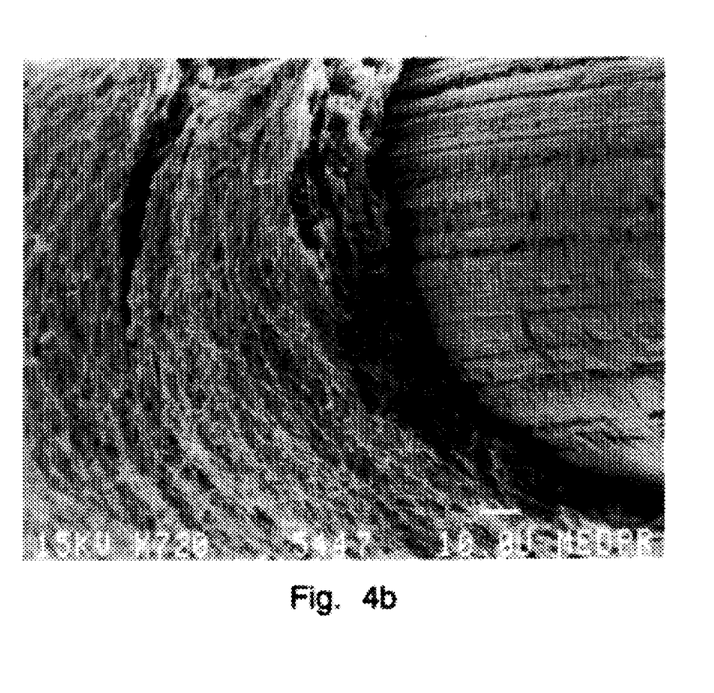
Figure 4C:
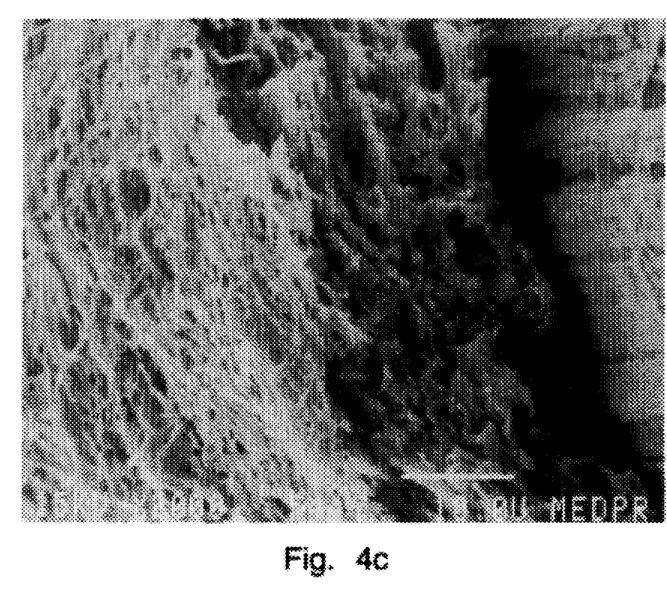

Stents were rotated 5/16 of a turn after each burst and sprayed initially with 50 bursts/end. After at least 4 hours of air drying, the stents were fixtured at the other end and the second half was coated. After overnight vacuum drying at 80° C., the stents were weighed. Additional coatings were applied using the same conditions to bring each stent up to the target weight. The completed stents were vacuum dried at 80° C. for 7 days. The stents were tested for mechanical adhesion of the coating during crimping and expansion operations. The coating was finally fractured by straightening out the sinusoidal wave of the stent and the coating was pulled off with a tweezers to produce the SEM micrographs shown on FIGS. 4a–4c of the coating at 180X, 720X and 2000X respectively.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A method for providing a therapeutic substance into a body lumen comprising the steps of:
   (a) providing a cylindrical, radially expandable stent body;
   (b) applying to the stent body a solution which includes a solvent, a polymer dissolved in the solvent and a therapeutic substance dispersed in the solvent;
   (c) evaporating the solvent;
   (d) repeating application and evaporating steps (b) and (c) to provide an amount of polymer and a specified dose of therapeutic substance on the stent body;
   (e) applying to the polymer and therapeutic substance on the stent body an overlayer of the polymer by the steps of:
      (1) applying to the stent body a solution which includes the solvent and the polymer dissolved in the solvent while maintaining the specified dose of therapeutic substance applied in steps (a) to (d) on the stent;
      (2) evaporating the solvent; and
      (3) repeating application and evaporating steps (1) and (2) to provide a thickness of polymer on the stent body; and
   (f) radially expanding the stent body, applied polymer and therapeutic substance such that the polymer and therapeutic substance are retained on the stent body.

2. A method according to claim 1 wherein the overlayer is applied by spraying.

3. A method according to claim 1 wherein the overlayer is applied by immersion.

4. A method according to claim 1 wherein the polymer is a bioabsorbable polymer.

5. A method according to claim 4 wherein the polymer is selected from the group consisting of poly(lactic acid), poly(lactide-co-glycolide) and poly(hydroxybutyrate-co-valerate).

6. A method according to claim 1 wherein the polymer is a biostable polymer.

7. A method according to claim 6 wherein the polymer is selected from the group consisting of silicones, polyurethanes, polyesters, vinyl homopolymers and copolymers, acrylate homopolymers and copolymers, polyethers and cellulosics.

8. A method according to claim 1 wherein the solution for applying the overlayer further includes a second solvent in which the polymer has a lesser solubility.

9. A method according to claim 1 wherein the drug is selected from the group consisting of glucocorticoids, dexamethasone, dexamethasone sodium phosphate, anticoagulants, heparin, hirudin, tick anticoagulant peptide, angiopeptin, antimitotic agents, and oligonucleotides.

10. A method for making an intravascular stent comprising the steps of:

(a) providing a cylindrical, radially expandable stent body;

(b) applying to the stent body a solution which includes a solvent, a polymer dissolved in the solvent and a therapeutic substance dispersed in the solvent;

(c) evaporating the solvent;

(d) repeating application and evaporating steps (b) and (c) to provide an amount of polymer and therapeutic substance on the stent body;

(e) eluting a known portion of the therapeutic substance from the polymer in an aqueous solution until a specified dose of the therapeutic substance is present on the stent; and (f) radially expanding the stent body, applied polymer and therapeutic substance after elution such that the polymer and therapeutic substance are retained on the stent body.

11. A method according to claim 10 wherein the polymer is selected from the group consisting of poly(L-lactic acid), poly(lactide-co-glycolide), fibrin, silicone, polyurethane, and poly(phosphoester urethane).

* * * * *